United States Patent [19]

Donovan

[11] Patent Number: 4,822,886

[45] Date of Patent: Apr. 18, 1989

[54] CYCLIC N-HYDROXYIMIDES

[75] Inventor: Stephen F. Donovan, Fairfield, Conn.

[73] Assignee: American Cyanamid Company, Stamford, Conn.

[21] Appl. No.: 84,239

[22] Filed: Aug. 12, 1987

[51] Int. Cl.$^4$ ............... C07D 207/416; C07D 211/94
[52] U.S. Cl. .................................... 546/243; 548/542
[58] Field of Search .......................... 548/542; 546/243

[56] References Cited

U.S. PATENT DOCUMENTS 2,695,905  11/1954  Eilar .................................... 548/544
4,161,590  9/1979  Mueller ............................. 548/544

Primary Examiner—David B. Springer
Attorney, Agent, or Firm—Steven H. Flynn

[57] ABSTRACT

Cyclic N-hydroxyimide compounds are disclosed which show strong metal ion chelating properties and are useful as detergent additives. Detergent compositions containing the N-hydroxyimides improve the stain removing effectiveness of detergents and are biodegradable.

4 Claims, No Drawings

CYCLIC N-HYDROXYIMIDES

The present invention relates to a new class of chelating agents which are useful, e.g., as additives to detergent compositions, particularly fabric-washing detergent compositions. In particular it relates to new cyclic N-hydroxyimides and salts thereof useful as detergent additives and to detergent compositions comprising at least one detersive surfactant and an effective amount of an N-hydroxyimide detergent additive.

BACKGROUND OF THE INVENTION

Detergent compositions have long employed materials, known as "builders", to improve the detergency of soaps and synthetic detergents by actively chelating alkali metal cations which are normal components of "hard" tap water. Such builders have been found to affect, for instance, soil suspension, emulsification of soil particles, solubilization of water-insolubles, and inactivation of various mineral constituents present in a detergent system. Many materials useful as builders have been proposed, and their effects are known. See, e.g., U.S. Pat. No. 3,852,213, U.S. Pat. No. 3,950,260, U.S. Pat. No. 4,182,718, and U.S. Pat. No. 4,440,646 (all incorporated herein by reference).

Recently, however, the attention of detergent manufacturers and researchers has turned to the role of heavier metal cations, i.e., transition metal cations and particularly iron, in the formation of stain complexes on fabrics and other surfaces. It has been observed that these multivalent transiton metal cations, particularly iron ($Fe^{+++}$), enhance the binding of the components of many stains to substrates, and breaking up the cation-enhanced bonds is an effective approach to stain removal. Therefore, there is a strong need for the discovery of new materials that are effective as chelating agents for transition metal cations, are easy to prepare, and can be added to detergent compositions in economical amounts to boost stain-removing power.

It has now been discovered that certain cyclic N-hydroxyimides derived from citric acid esters are active transition metal ion chelants, particularly with respect to iron ($Fe^{+++}$), making them attractive as additives for detergent compositions to aid in stain removal. In addition, the N-hydroxyimides of the present invention are believed to be broken down in freshwater systems to citric acid, which is well known to be biodegradable.

SUMMARY OF THE INVENTION

It is therefore an object of the present invention to provide a new class of compounds having strong transition metal ion chelating properties.

It is a further object of the present invention to provide a detergent additive useful against stains.

It is a further object of the present invention to provide a detergent additive that is biodegradable.

It is a further object of the present invention to provide a novel detergent composition.

It is a further object of the present invention to provide a fabric-washing detergent composition that is effective in stain removal.

It is a further object of the present invention to provide a method for preparing chelating agents showing activity in basic aqueous solutions.

These and other objects are achieved, according to the present invention, by detergent builders consisting essentially of cyclic N-hydroxyimides having the formula

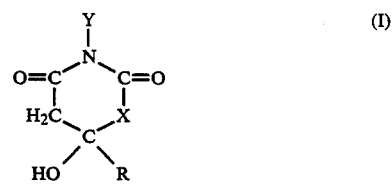

wherein X is either —$CH_2$— or a direct bond to the adjacent ring carbon (ring position no. 2), provided that where X is —$CH_2$—, R is —COOH or an alkali metal or ammonium salt thereof, and where X is the direct bond, R is either —$CH_2$—COOH or $CH_2$CO—NHOH, or alkali metal or ammonium salts thereof, and where Y is —OH or —$O^-M^+$, where $M^+$ is an alkali metal or ammonium cation.

Also contemplated herein are detergent compositions comprising one or more detersive surfactants and one or more cyclic N-hydroxyimides having the formula

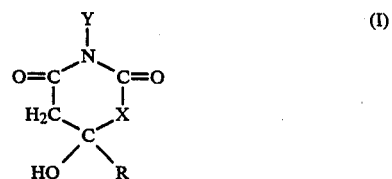

where R, X, and Y have the same meaning as above.

Also contemplated herein is a detergent builder intermediate composition comprising a mixture of carboxylic acid-functional or hydroxamic acid-functional cyclic N-hydroxyimide compounds selected from the group consisting of:

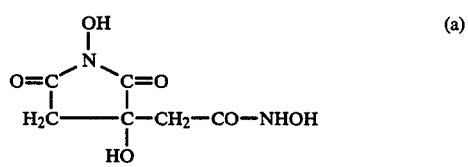

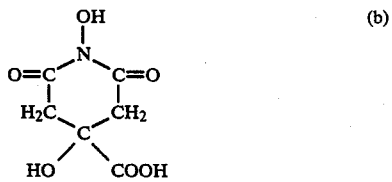

and

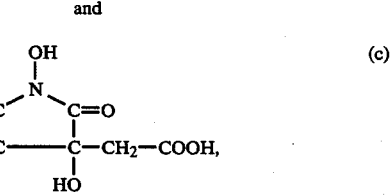

or alkali metal or ammonium salts thereof.

Also contemplated is a liquid detergent comprising an aqueous solution having a basic pH comprising one or more detersive surfactants and one or more detergent additives of the formula

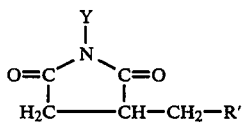

wherein R' is —COOH or an alkali metal salt thereof, and Y is —OH or —O⁻M⁺, where M⁺ is an alkali metal or ammonium cation.

DETAILED DESCRIPTION OF THE INVENTION

The N-hydroxyimide compounds of the present invention are advantageously prepared from citric acid by first reacting it with an alkanol to form a citrate ester. These esters are then reacted with hydroxylamine to obtain the N-hydroxyimides of the present invention. A mixture of N-hydroxyimides is initially formed by this reaction at neutral or acidic pH, but in aqueous solutions at basic pH (i.e., above about pH 9), the product is predominantly the 3-carbomethoxy-1,3-dihydroxy-2,5-pyrrolidinedione (or an alkali metal salt or disalt thereof). Thus, a typical reaction scheme for the preparation of detergent builders according to the present invention is as follows:

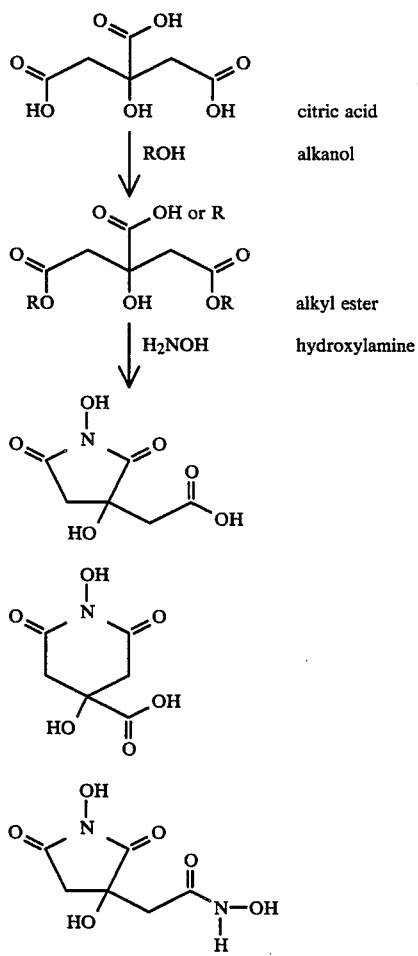

Citric acid (2-hydroxy-1,2,3-propanetricarboxylic acid) occurs naturally in plant and animal tissues and is produced on an industrial scale by fermentation of sugars or extraction from citrus fluids (e.g., lemon juice, pineapple wastes). Citric acid is usually obtained as the monohydrate ($C_6H_8O_7 \cdot H_2O$), which is a crystalline solid at room temperature.

In order to prepare the alkyl citrate esters which are intermediates in preparing the N-hydroxyimide compounds of the present invention, citric acid monohydrate is first dehydrated to eliminate the water of crystallization. This may be easily accomplished by heating at moderate temperatures, e.g., 40°–50° C. Preferably, the citric acid monohydrate is suspended in a hydrocarbon solvent such as petroleum ether, preferably 30°–60° C. petroleum ether, and the water removed as a low boiling azeotrope and the petroleum ether decanted from the crystalline product. Thereafter, the anhydrous citric acid is reacted with an alkanol of from 1 to 6 carbons, e.g., methanol, ethanol, propanol, isopropanol, butanol, isobutanol, etc.

The amount of alkanol employed will normally be a large stoichiometric excess in order to ensure esterification of at least 2 of the 3 carboxyl groups of the tricarboxylic acid substrate. Most advantageously, the citric acid is simply dissolved in a suitable quantity of the alkanol, e.g., 2–20 moles alkanol per mole of citric acid. The mixture is preferably acidified by the addition of an acid such as sulfuric acid. The product crystallizes in the alkanol solution and is easily filtered, washed and dried. A method similar to the foregoing is set forth in Hirota et al, *Chemical Letters,* 191–4 (1980), which is incorporated herein by reference.

Reaction of the alkyl citrate ester to obtain N-hydroxyimide products may be accomplished by contacting the ester with at least a substantially equimolar quantity of hydroxylamine, $H_2NOH$. Salts of hydroxylamine may be used, such as hydroxylamine hydrochloride, in which case the reaction will normally be carried out in the presence of about 2–5 moles per mole of hydroxylamine of a basic agent, preferably an organic base such as sodium ethoxide, pyridine, triethylamine, or quinoline. Most preferably, the reaction will be carried out in an alcoholic solvent, such as ethanol. The reaction takes place at room temperature and is completed in several hours, e.g., 2–20 hours.

The product may be isolated in any one of a number of known ways. For example, the product can be isolated by precipitation from a non-solvent, such as hexanes, and the precipitate filtered, washed and dried under vacuum to give the cyclic N-hydroxyimide product.

Alternatively, flash or spray drying may be used. The drying step removes substantially all of the organic base, and washing with alcoholic hydrogen chloride effectively scavenges residual amounts, in cases where complete removal of the basic agent is required.

The cyclic N-hydroxyimide compounds are active metal ion chelants and are advantageously included in a detergent composition to boost stain removal, in accordance with the present invention. A detergent composition of this invention will contain at least one detersive surfactant. Such surfactants will be present in amounts usually encountered in detergent compositions, e.g., from about 1 to about 50% by weight, preferably about 5 to about 25% by weight for fabric-washing detergents, and most preferably from about 10 to about 20% by weight based on the total weight of the detergent composition. The surfactants may be anionic, nonionic, cationic or amphoteric, and mixtures of different detersive surfactants may be used. Non-limiting examples of suitable detersive surfactants include:

(a) Anionic surfactants: soaps, i.e., alkali metal (preferably sodium or potassium) salts of long-chain fatty acids containing from 8 to 20 carbon atoms, such as lauric, myristic, oleic, palmitic, capric, caprylic, and stearic acids, used singly or in mixtures of differing chain lengths; alkali metal salts of organic sulfuric reaction products having long hydrocarbon chains of about 8 to about 20 carbon atoms and a radical selected from the group consisting of sulphonic acid and sulfuric acid ester radicals, such as sodium or potassium alkyl sulphates, preferably those obtained by sulphating higher ($C_8$–$C_{18}$) alcohols; sodium or potassium alkyl benzenesulphonates in which the alkyl group contains from about 9 to about 20 carbon atoms, such as sodium linear alkyl ($C_{10}$–$C_{15}$) secondary benzenesulphonate, 2-phenyl-dodecanesulphonate, 2-phenyl-octadecanesulphonate and 3-phenyl-dodecanesulphonate; alkali metal (preferably sodium) olefin sulphonates, i.e., the mixture of detersive surfactants obtained from sulphonation of $C_8$–$C_{22}$ olefins, preferably straight-chain alpha-olefins; sodium alkyl glyceryl ether sulphonates, including ethers of higher alcohols derived from tallow coconut oil and synthetic alcohols derived from petroleum; sodium coconut oil fatty acid monoglyceride sulphates and sulphonates; sodium or potassium salts of sulfur acid esters of the reaction between higher fatty alcohols (e.g., tallow or coconut oil alcohols) and ethylene oxide; the esterification products of fatty acids with isethionic acid, neutralized with sodium hydroxide; and sodium or potassium salts of fatty acid amides of methyl taurine.

(b) Nonionic synthetic detersive surfactants: compounds formed by condensing ethylene oxide with a hydrophobic base formed by the condensation of propylene oxide with propylene glycol; the polyethylene oxide condensates of alkyl-phenols, e.g., the condensation products of alkylphenols, having an alkyl group containing from about 6 to 12 carbon atoms in either a straight or branched chain, with ethylene oxide, said ethylene oxide being present in amounts equal to 5 to 25 moles of ethylene oxide per mole of alkylphenols (the alkyl substituent in such compounds may be derived from polymerised propylene, diisobutylene, octene, dodecene, or nonene, for example); compounds derived from the condensation of ethylene oxide with the product resulting from the reaction of propylene oxide and ethylenediamine, such as compounds containing from about 40% to about 80% polyoxyethylene by weight and having a molecular weight of from about 5,000 to about 11,000 resulting from the reaction of ethylene oxide groups with a hydrophobic base constituted of the reaction product of ethylenediamine and excess propylene oxide, said hydrophobic base having a molecular weight of the order of 2,500 to 3,000; the condensation product of aliphatic alcohols having from 8 to 18 carbon atoms, in either straight chain or branched chain configuration, with ethylene oxide, e.g., a coconut alcohol-ethylene oxide condensate having from 6 to 30 moles of ethylene oxide per mole of coconut alcohol, the coconut alcohol fraction having from 10 to 14 carbon atoms; long chain tertiary amine oxides corresponding to the following general formula, $R^1R^2R^3N=O$, wherein $R^1$ is an alkyl radical of from about 8 to 18 carbon atoms and $R^2$ and $R^3$ are each methyl, ethyl or hydroxyethyl radicals, such as dimethyldodecylamine oxide, dimethyloctylamine oxide, dimethyldecylamine oxide, diethyltetradecylamine oxide and dimethylhexadecylamine oxide, N-bis(hydroxyethyl)dodecylamine oxide; long chain tertiary phosphine oxides corresponding to the following formula $R^4R^5R^6P=O$, wherein $R^4$ is an alkyl, alkenyl or monohydroxyalkyl radical of 10 to 18 carbon atoms and $R^5$ and $R^6$ are each alkyl or monohydroxyalkyl groups containing from 1 to 3 carbon atoms, such as dimethyldodecylphosphine oxide, dimethyltetradecylphosphine oxide, ethylmethyltetradecylphosphine oxide, cetyldimethylphosphine oxide, dimethylstearylphosphine oxide, cetylethylpropylphosphine oxide, diethyldodecylphosphine oxide, diethyltetradecylphosphine oxide, bis(hydroxymethyl)dodecylphosphine oxide, bis(2-hydroxyethyl)dodecylphosphine oxide, 2-hydroxypropylmethyltetradecylphosphine oxide, dimethyloleylphosphine oxide, and dimethyl-2-hydroxydodecylphosphine oxide; and dialkyl sulphoxides corresponding to the following formula, $R^7R^8S=O$, wherein $R^7$ is an alkyl, alkenyl, beta- or gamma-monohydroxyalkyl radical or an alkyl or beta- or gamma-monohydroxyoxyalkyl radical containing one or two other oxygen atoms in the chain, the $R^7$ groups ranging from 10 to 18 carbon atoms in chain length, and wherein $R^8$ is methyl, ethyl or alkylol, such as dodecyl methyl sulphoxide, tetradecyl methyl sulphoxide, 3-hydroxytridecyl methyl sulphoxide, 2-hydroxydodecyl methyl sulphoxide, 3-hydroxy-4-decyloxybutyl methyl sulphoxide, 3-hydroxy-4dodecyloxybutyl methyl sulphoxide, 2-hydroxy-3-decyloxypropyl methyl sulphoxide, 2-hydroxy-3-dodecyloxypropyl methyl sulphoxide, dodecyl ethyl sulphoxide, 2-hydroxydodecyl ethyl sulphoxide, dodecyl-2-hydroxy ethyl sulphoxide.

(c) Ampholytic synthetic surfactants: derivatives of aliphatic secondary and tertiary amines, in which the aliphatic radical may be straight chain or branched chain and wherein one of the aliphatic substituents contains from about 8 to 18 carbon atoms and one contains an anionic water solubilizing group, such as sodium-3-dodecylaminopropionate, sodium-3-dodecylaminopropanesulphonate and sodium N-2-hydroxydodecyl-N-methyl-taurate.

(d) Zwitterionic synthetic surfactants: derivatives of aliphatic quaternary ammonium compounds, sulphonium compounds and phosphonium compounds in which the aliphatic radical may be straight or branched chain and wherein one of the aliphatic substituents contains from about 8 to 18 carbon atoms and one contains an anionic water solubilizing group, such as 3-(N,N-dimethyl-N-hexadecylammonio)propane-1-sulphonate, 3-(N,N-dimethyl-N-hexadecylammonio)-2-hydroxy-propane-1-sulphonate, 3-(dodecylmethylsulphonium)-propane sulphonate, and 3-(cetylmethylphosphonium)ethane sulphonate.

The detergent compositions of the present invention will contain, besides one or more detersive surfactants, about 3% to about 12% by weight of the composition, preferably about 6% by weight, of the cyclic N-hydroxyimide compounds described above.

In addition to the surfactants and the N-hydroxyimide compounds, the detergent composition may also contain conventional detergent builders such as condensed phosphates, trisodium nitrilotriacetate (NTA), sodium carbonate, zeolites, sodium silicates, etc., and organic polymers such as polyacrylates, polymaleates and polymethacrylates. See, e.g., U.S. Pat. No. 3,393,150, U.S. Pat. No. 3,666,664, U.S. Pat. No. 3,707,502, U.S. Pat. No. 3,839,215 and U.S. Pat. No.

4,067,816, which are incorporated herein by reference. The combined detergent builders will make up from about 10% to about 50% by weight of the detergent composition. In addition to the essential detersive surfactants and detergent additives, a detergent composition of the invention may comprise such conventional ingredients as lather boosters (e.g., alkanolamides), fillers, antiredeposition agents, fluorescers, pigments, germicides, scents, and enzymes.

A detergent composition according to the invention can be prepared by any conventional manufacturing technique used for preparing detergent compositions, such as slurry making and spray-drying, and the detergent can take anyone of the common physical forms associated with detergents, such as powders, flakes, granules, noodles, cakes, bars and liquids.

Liquid detergent compositions according to the invention will most preferably be a concentrated aqueous solution having a basic pH, at least about pH8, comprising one or more of the detersive surfactants described above and one or more cyclic N-hydroxyimide compounds of this invention. In basic solution, as discussed previously, it has been observed that the mixed N-hydroxyimide compounds formed initially by reacting an alkyl citrate ester and hydroxylamine undergo a substantially complete conversion to a single carboxyfunctional species. Therefore, the most preferred liquid detergent composition according to the invention will comprise a concentrated aqueous solution having a basic pH, preferably pH 9-pH 12, one or more detersive surfactants, and at least one cyclic N-hydroxyimide compounds of the formula

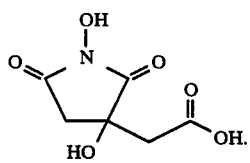

Alkali metal and ammonium salts and disalts are also contemplated.

The invention is further illustrated by the following examples, which should not be construed as limiting the scope of the invention.

EXAMPLE 1

Preparation of Sym-Dimethyl Citrate 204 g (0.971 moles) of citric acid monohydrate and 500 ml of 30°-60° C. petroleum ether were placed in a reaction vessel and refluxed overnight. A total of 23 ml of water were collected. The petroleum ether was decanted, then 500 ml of absolute methanol (12.48 moles) and 6 ml of sulfuric acid (0.113 moles) were added.

The reaction mixture was stirred at room temperature for 6 days, with the formation of white crystals. The crystals were filtered and washed with 100 ml of diethyl ether, then dried at 5 mm Hg in a rotary evaporator.

171.5 g of white crystals, m.p. 116°-120° C., were obtained. Nuclear magnetic resonance (NMR) analysis confirmed the sym-dimethyl citrate structure.

EXAMPLE 2

N-Hydroxyimide Derivative of Sym-Dimethyl Citrate

An alcoholic hydroxylamine/sodium ethoxide reactant solution was prepared as follows: 10 g (0.43 moles) of metallic sodium were added to 250 ml of absolute ethanol under nitrogen gas. A separate hydroxylamine solution was prepared by adding 15 g (0.217 moles) of hydroxylamine hydrochloride to 300 ml of absolute ethanol. The two solutions were mixed at 40° C., then cooled to 0° and filtered.

23.8 g (0.1 moles) of the sym-dimethyl citrate of Example 1 were dissolved in 100 ml ethanol and added to the hydroxylamine/sodium ethoxide solution. The reaction mixture was allowed to stand at room temperature overnight, with the formation of a white precipitate.

400 ml of hexane was added to the reaction mixture, which was then filtered. The white solid was dissolved in 500 ml of water, filtered through Celite ® (Johns-Manville) and freezed dried to give 39.63 g of a light yellow powder.

The above procedure was repeated exactly and the solid products combined to give a total of 63.9 g of a light yellow powder.

Infrared (IR), NMR, and high pressure liquid chromatography (HPLC, with UV detector set at 270 nm) indicated a mixture of 3 species:

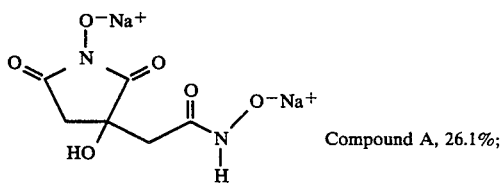

Compound A, 26.1%;

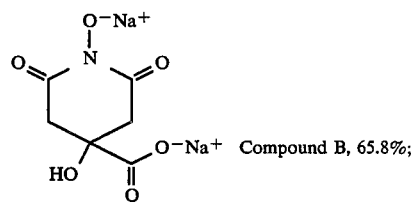

Compound B, 65.8%;

and

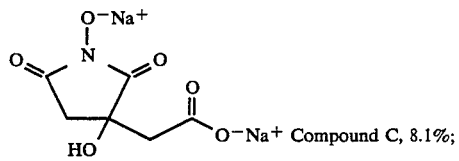

Compound C, 8.1%;

EXAMPLE 3

N-Hydroxyimide Derivative of Triethyl Citrate

An alcoholic solution of hydroxylamine/sodium ethoxide was prepared as in Example 2, using 15 g (0.65 moles) sodium in 300 ml absolute ethanol, and 22.5 g (0.324 mole) hydroxylamine hydrochloride in 500 ml absolute ethanol. To the filtered hydroxylamine/sodium ethoxide solution was added 30 g (0.109 mole) of triethyl citrate. The reaction mixture was allowed to stand at room temperature overnight, with formation of a white precipitate.

400 ml of hexane was added to the reaction mixture and the mixture filtered. The white solid obtained was then dissolved in 500 ml water and filtered through Celite ®. The filtrate was freeze dried to give 38.15 g of a light yellow powder.

IR, NMR, and HPLC-UV analysis indicated a mixed product having the same three components as obtained in Example 2: 57.3% of Compound A, 15.0% of Compound B, and 27.7% of Compound C.

When the above mixed product was maintained in an alkaline solution at room temperature, HPLC-UV analysis indicated that the relative amounts of Compounds A and B decreased over time, with a concomitant increase in the amount of Compound C.

EXAMPLE 4

N-Hydroxyimide Derivative of Triethyl Citrate

An alcoholic hydroxylamine/sodium ethoxide solution was prepared as in previous examples using 10 g sodium added to 250 ml ethanol under nitrogen gas. The sodium ethoxide solution was added to 15 g of hydroxylamine hydrochloride in 300 ml ethanol at 40° C. and cooled to 0° C., then filtered.

20.0 g triethyl citrate was added to the hydroxylamine/sodium ethoxide solution at 5° C., and this mixture was allowed to stand overnight at room temperature.

400 ml hexane was added to the reaction mixture, which was then filtered and the solid product dried overnight under high vacuum. The solid product was combined with 500 ml of water, filtered through Celite ®, partially dried in a rotary evaporator and freeze dried to give 19.94 g of a yellowish powder.

EXAMPLE 5

Hydrolysis of Triethyl Citrate Derivative

An alcoholic hydroxylamine/sodium ethoxide solution was prepared as in previous examples using 15 g of sodium in 300 ml of absolute ethanol. This solution was added to 22.5 g of hydroxylamine hydrochloride in 500 ml absolute ethanol at 40° C. The reaction mixture was then cooled to 5° C. and filtered.

70 g of triethyl citrate was added to the hydroxylamine/sodium ethoxide solution and the mixture allowed to stand at room temperature overnight, with formation of a white precipitate. 250 ml of water were added, and the ethanol was removed by rotary evaporator at reduced pressure. 300 ml additional water were added and the solution warmed to 50° C.

Sodium hydroxide pellets were added to the solution until the pH stabilized at 10.5. The reaction mixture was stirred overnight at 80° C., then cooled. The final pH was 10.1.

300 ml of diethyl ether were added to the mixture, which was shaken and allowed to separate into ether and aqueous layers. The ether layer was decanted and discarded; the aqueous layer was partially dried in a rotary evaporator and the product freeze dried to yield 72.3 g of a light yellow powder.

IR, NMR, HPLC and HPLC-UV analysis indicated 98.6% of the product to have the formula of Compound C (with 0.7% Compound B, no Compound A, and 0.7% unknown).

EXAMPLE 6

Tea Stain Removal Test

The performance of the cyclic N-hydroxyimide compounds as fabric-washing detergent additives was examined in a tea stain removal test:

Swatches of white cotton cloth were boiled in very strong tea (10 tea bags /1 liter dionized water, brewed 10 min.) for 15 minutes. The tea solution and swatches were removed from the heat and cooled to 115° F. with continued stirring. The swatches were thereafter wrung and air dried between paper towels.

Deionized water was heated to 40° C. and 0.1 g of $CaCl_2$ were added per each liter of water, followed by 1.5 g per liter of water of a commercial fabric-washing detergent (Tide ®; Procter & Gamble).

To 1-liter aliquots of this detergent solution were added 100 mg of the detergent additives to be tested, which were stirred until dissolved. The wash solutions were maintained at about 35° C. and a stirring speed of 100 rpm. The pH was adjusted to 10 if necessary with sulfuric acid or sodium hydroxide. Tea stained swatches of cloth were added to each test solution and stirred rapidly for 10 minutes, after which the solution was poured off and the swatches squeezed out and rinsed for 2 minutes in deionized water containing the same proportion of $CaCl_2$. The swatches were then air dried overnight and compared against a control and a commercial detergent additive.

Samples of the cyclic N-hydroxyimides of Examples 2, 4 and 5 were tested against a control detergent solution (no additives) and against a commercial detergent additive (Dequest ®2041; Monsanto). After washing swatches in the respective solutions as described above, the control detergent sample appeared darkest and the comparison sample and samples using the compounds of the foregoing examples appeared significantly lighter.

It will be understood that the foregoing description of the invention is susceptible to modifications, changes and adaptations, all of which are intended to be comprehended within the meaning and range of equivalents of the appended claims. For instance, though the foregoing description is directed to the use of the N-hydroxyimides in detergent systems, they will also find application in boiler water systems and other scale prevention uses, polymerization intermediates, and other embodiments where strong metal ion chelation is required.

I claim:

1. N-hydroxyimide compounds having the formula

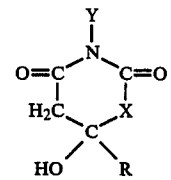

wherein X is either —$CH_2$— or a direct bond to the adjacent ring carbon, provided that where X is —$CH_2$—, R is —COOH or an alkali metal or ammonium salt thereof, and where X is the direct bond, R is either —$CH_2$—COOH or —$CH_2$—CO—NHOH, or an alkali metal or ammonium salt thereof, and where Y is —OH or —O$^-$M$^+$, where M$^+$ is an alkali metal or ammonium cation.

2. A compound according to claim 1, wherein X is a direct bond and R is —$CH_2$—CO—NHO$^-$Na$^+$.

3. A compound according to claim 1, wherein X is —$CH_2$— and R is —COO$^-$Na$^+$.

4. A compound according to claim 1, wherein X is a direct bond and R is —$CH_2$—COO$^-$Na$^+$.

* * * * *